United States Patent [19]
Lessar et al.

[11] Patent Number: 5,902,326
[45] Date of Patent: May 11, 1999

[54] OPTICAL WINDOW FOR IMPLANTABLE MEDICAL DEVICES

[75] Inventors: Joseph F. Lessar, Coon Rapids; Keith A. Miesel, St. Paul; Susan A. Tettemer, Fridley; John C. Olson, Maple Grove, all of Minn.

[73] Assignee: Medtronic, Inc., Minneapolis, Minn.

[21] Appl. No.: 08/923,079

[22] Filed: Sep. 3, 1997

[51] Int. Cl.⁶ .................................................. A61N 1/375
[52] U.S. Cl. ............................................. 607/36; 600/333
[58] Field of Search ..................................... 600/372–374, 600/310, 377, 381, 393, 394, 325, 327, 333; 607/115, 119, 122, 36

[56] References Cited

U.S. PATENT DOCUMENTS

| | | |
|---|---|---|
| H1114 | 12/1992 | Schweitzer et al. . |
| 3,746,087 | 7/1973 | Lavering et al. . |
| 3,847,483 | 11/1974 | Shaw et al. . |
| 4,114,604 | 9/1978 | Shaw et al. . |
| 4,202,339 | 5/1980 | Wirtzfeld et al. . |
| 4,399,820 | 8/1983 | Wirtzfeld et al. . |
| 4,407,296 | 10/1983 | Anderson . |
| 4,421,386 | 12/1983 | Podgorski . |
| 4,444,498 | 4/1984 | Heinemann . |
| 4,523,279 | 6/1985 | Sperinde et al. . |
| 4,554,927 | 11/1985 | Fussell . |
| 4,623,248 | 11/1986 | Sperinde . |
| 4,651,741 | 3/1987 | Passafaro . |
| 4,697,593 | 10/1987 | Evans et al. . |
| 4,727,879 | 3/1988 | Liess et al. . |
| 4,750,495 | 6/1988 | Moore et al. . |
| 4,791,935 | 12/1988 | Baudino et al. . |
| 4,807,629 | 2/1989 | Baudino et al. . |
| 4,813,421 | 3/1989 | Baudino et al. . |
| 4,815,469 | 3/1989 | Cohen et al. . |
| 4,830,488 | 5/1989 | Heinze et al. . |
| 4,903,701 | 2/1990 | Moore et al. . |
| 5,005,573 | 4/1991 | Buchanan . |
| 5,040,533 | 8/1991 | Fearnot . |
| 5,040,538 | 8/1991 | Mortazavi . |
| 5,058,586 | 10/1991 | Heinze . |
| 5,067,960 | 11/1991 | Grandjean . |
| 5,113,862 | 5/1992 | Mortazavi . |
| 5,176,138 | 1/1993 | Thacker . |
| 5,267,564 | 12/1993 | Barcel et al. . |
| 5,312,454 | 5/1994 | Roline et al. . |
| 5,329,922 | 7/1994 | Atlee, III . |
| 5,358,519 | 10/1994 | Grandjean . |
| 5,411,532 | 5/1995 | Mortazavi . |
| 5,438,987 | 8/1995 | Thacker et al. . |
| 5,490,323 | 2/1996 | Thacker et al. . |
| 5,535,752 | 7/1996 | Halperin et al. . |
| 5,564,434 | 10/1996 | Halperin et al. . |
| B1 4,467,807 | 6/1992 | Bornzin . |

FOREIGN PATENT DOCUMENTS

WO 80/01620  8/1980  WIPO .

*Primary Examiner*—William E. Kamm
*Assistant Examiner*—Carl H. Layno
*Attorney, Agent, or Firm*—Thomas F. Woods; Harold R. Patton

[57] ABSTRACT

An optical window assembly for use in implantable medical devices includes a generally U-shaped ferrule having a strain relief channel to accommodate residual stresses remaining in the ferrule after welding the ferrule to the housing of an implantable medical device. The assembly may be used to transmit optical energy and/or electrically insulate a feedthrough. The assembly can be mounted in a window opening in a housing. The ferrule can include a ferrule body forming a lens opening, the ferrule body having a generally U-shaped cross-section with an inner leg, an outer leg, and a strain relief channel in the ferrule body between the inner leg and the outer leg. A lens is mounted in the lens opening of the ferrule. The ferrule can also include a lens flange on the inner leg of the ferrule body, a support flange on the outer leg of the ferrule body, and/or a braze stop to control flow of the braze. The ferrule and housing can be constructed of titanium. Also disclosed are methods of manufacturing the optical window assemblies and implantable medical devices including the optical window assemblies.

35 Claims, 6 Drawing Sheets

OPTICAL WINDOW FOR IMPLANTABLE MEDICAL DEVICES

BACKGROUND OF THE INVENTION

Ceramics and glasses are used in implantable medical devices for a variety of purposes. In some instances, optical windows including ceramics or glasses are used to transmit optical energy in vivo either into the device or out of the device to monitor or detect a variety of conditions or parameters. In other cases, optical windows including ceramics or glasses are used to provide an electrically insulated point of entry into the device for, e.g., a feedthrough pin used to deliver electrical signals or energy between the interior and exterior of the device.

When used for transmitting optical energy, it is important that the optical window assembly be capable of transmitting light of the desired wavelengths. One example of an implantable medical device using optical energy is a blood oxygen sensor. In some instances, the sensors are located along the lead of, e.g., a pacemaker. By incorporating a blood oxygen sensor into an implantable cardiac pacemaker, the patient's blood oxygen saturation level can be monitored and used as one factor in setting the pacemaker's rate.

Like any device designed for implantation, implantable medical devices incorporating optical windows must be made of biocompatible and biostable materials. In addition, devices must also be hermetically sealed to protect the components within the implantable device from contamination. In the case of a blood oxygen sensor designed for long-term placement in a blood environment, the design also preferably provides smooth outer surfaces to minimize the formation of clots and other undesirable events.

Attempts at providing optical transmission into and out of implantable medical devices such as blood oxygen sensors located in leads has included providing the optical sensors or sources enclosed in glass or sapphire tubes and other structures. Enclosing the devices within a tube presents a number of problems in the manufacture of such devices. In addition, it is often difficult to provide a long-term hermetic seal to prevent contamination of the devices by body fluids.

Where optical windows including ceramics or glasses are used to electrically insulate, e.g., a feedthrough pin, it is advantageous to use a window formed of material that is electrically non-conductive and that may also be optically transmissive. The optically transmissive characteristic can be useful because it allows for relatively easy visual inspection of the feedthrough assembly to determine whether any cracks are present in the lens (i.e., insulating) material that could compromise hermeticity of the device.

Although not admitted as prior art, examples of implantable medical devices incorporating optically transmissive portions, such as windows, etc., can be found in the published documents listed in Table 1 below.

| Patent/Document No. | Inventor(s) | Issue/Publication Date |
| --- | --- | --- |
| H1114 | Schweitzer et al. | December 1, 1992 |
| B1 4,467,807 | Bornzin | June 30, 1992 |
| 3,746,087 | Lavering et al. | July 17, 1973 |
| 3,847,483 | Shaw et al. | November 12, 1974 |
| 4,114,604 | Shaw et al. | September 19, 1978 |
| 4,202,339 | Wirtzfeld et al. | May 13, 1980 |
| 4,399,820 | Wirtzfeld et al. | August 23, 1983 |
| 4,407,296 | Anderson | October 4, 1983 |
| 4,421,386 | Podgorski | December 20, 1983 |
| 4,444,498 | Heinemann | April 24, 1984 |
| 4,523,279 | Sperinde et al. | June 11, 1985 |
| 4,554,977 | Fussell | November 26, 1985 |
| 4,623,248 | Sperinde | November 18, 1986 |
| 4,651,741 | Passafaro | March 24, 1987 |
| 4,697,593 | Evans et al. | October 6, 1987 |
| 4,727,879 | Liess et al. | March 1, 1988 |
| 4,750,495 | Moore et al. | June 14, 1988 |
| 4,791,935 | Baudino et al. | December 20, 1988 |
| 4,807,629 | Baudino et al. | February 28, 1989 |
| 4,813,421 | Baudino et al. | March 21, 1989 |
| 4,815,469 | Cohen et al. | March 28, 1989 |
| 4,830,488 | Heinze et al. | May 16, 1989 |
| 4,903,701 | Moore et al. | February 27, 1990 |
| 5,005,573 | Buchanan | April 9, 1991 |
| 5,040,538 | Mortazavi | August 20, 1991 |
| 5,058,586 | Heinze | October 22, 1991 |
| 5,067,960 | Grandjean | November 26, 1991 |
| 5,113,862 | Mortazavi | May 19, 1992 |
| 5,176,138 | Thacker | January 5, 1993 |
| 5,267,564 | Barcel et al. | December 7, 1993 |
| 5,312,454 | Roline et al. | May 17, 1994 |
| 5,329,922 | Atlee, III | July 19, 1994 |
| 5,358,519 | Grandjean | October 25, 1994 |
| 5,411,532 | Mortazavi | May 2, 1995 |
| 5,438,987 | Thacker et al. | August 8, 1995 |
| 5,490,323 | Thacker et al. | February 13, 1996 |
| 5,535,752 | Halperin et al. | July 16, 1996 |
| 5,564,434 | Halperin et al. | October 15, 1996 |
| WO 80/01620 | Kraska et al. | August 7, 1980 |

All patents listed in Table 1 above are hereby incorporated by reference in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

SUMMARY OF THE INVENTION

The present invention has certain objects, i.e., various embodiments of the present invention provide solutions to one or more problems existing in the prior art with respect to optically transmissive portions in implantable medical devices. Among the problems in the prior art is the lack of an optical window assembly designed for use with implantable medical devices that is: (a) capable of reducing residual tension stresses caused by welding of a ferrule to a device housing; and (b) which provides a low profile optical window assembly.

Accordingly, it is an object of the invention to provide an optical window assembly for a chronically implantable medical device that reduces welding stresses caused as a result of welding a ferrule to a device housing.

It is another object of the invention to provide an optical window assembly incorporating a lens and ferrule that provides a low profile optical window for use in implantable medical devices.

In comparison to known optical window assemblies for implantable medical devices, various embodiments of the present invention may provide one or more of the following advantages: (a) reduction or elimination of residual tension stresses imposed on a lens located in a ferrule in an optical window assembly for an implantable medical device; (b) a low profile, hermetically sealed optical window assembly for use in an implantable medical device; (c) ease of manufacturing using known methods and techniques such as brazing and welding; and (d) the use of known biostable and biocompatible materials.

Optical window assemblies in embodiments of the invention may include one or more of the following features: (a) a housing having a window opening; (b) a ferrule mounted in a window opening, the ferrule including a ferrule body forming a lens opening, the ferrule body having a generally U-shaped cross-section with an inner leg, an outer leg, and a strain relief channel in the ferrule body between the inner leg and the outer leg, wherein outer leg of the ferrule body is proximate the window opening of the housing; (c) a lens mounted in the lens opening of the ferrule; (d) a lens flange on the inner leg of the ferrule body; (e) a support flange on the outer leg of the ferrule body; (f) a support flange welded to the window opening; (g) a lens mounted in the lens opening with brazing; (h) a braze stop to control flow of the braze; (i) a titanium ferrule body; (j) a titanium housing; (k) a blood oxygen sensor housing; (l) a substantially circular window opening; (m) an inner leg and outer leg concentrically located about the lens opening; (n) a strain relief channel concentric with the inner and outer legs; and (o) a single crystal aluminum oxide lens.

Methods of manufacturing optical window assemblies for chronically implantable medical devices may include one or more of the following steps: (a) providing a ferrule having a ferrule body forming a lens opening, the ferrule body having a generally U-shaped cross-section with an inner leg, an outer leg, and a strain relief channel in the ferrule body between the inner leg and the outer leg, wherein the outer leg of the ferrule body is proximate the window opening of the housing; (b) providing a lens flange on the inner leg of the ferrule body; (c) providing a support flange on the outer leg of the ferrule body; (d) mounting a lens in the lens opening of the ferrule; (e) mounting the ferrule and lens in a window opening in a housing of an implantable medical device; (f) mounting the lens in the ferrule by brazing; (g) mounting the ferrule in the window opening in the housing by welding; (h) mounting the lens in the ferrule for mounting the ferrule in the window opening in the device housing; and (i) mounting the ferrule in a window opening of a blood oxygen sensor housing.

Implantable medical devices including an optical window assembly in embodiments present invention may include one or more of the following features: (a) a housing having a window opening; (b) a ferrule mounted in a window opening, the ferrule including a ferrule body forming a lens opening, the ferrule body having a generally U-shaped cross-section with an inner leg, an outer leg, and a strain relief channel in the ferrule body between the inner leg and the outer leg, wherein outer leg of the ferrule body is proximate the window opening of the housing; (c) a lens mounted in the lens opening of the ferrule; (d) a lens flange on the inner leg of the ferrule body; (e) a support flange on the outer leg of the ferrule body; (f) a support flange welded to the window opening; (g) a lens mounted in the lens opening with brazing; (h) a braze stop to control flow of the braze; (i) a titanium ferrule body; (j) a titanium housing; (k) a blood oxygen sensor housing; (I) a substantially circular window opening; (m) an inner leg and outer leg concentrically located about the lens opening; (n) a strain relief channel concentric with the inner and outer legs; and (o) a single crystal aluminum oxide lens.

These and other objects, advantages, and features of the invention will be apparent upon review of the Detailed Description of the Preferred Embodiments, the Drawings, and Claims appended hereto.

DETAILED DESCRIPTION OF THE PREFERRED EMBODIMENTS

The present invention provides an optical window assembly for use in implantable medical devices including a generally U-shaped ferrule having a strain relief channel to accommodate residual stresses remaining in the ferrule after welding the ferrule to the housing of an implantable medical device. By controlling residual stresses, the hermeticity of the optical window assembly can be maintained by reducing or eliminating cracks formed in the lens caused by residual stresses. An additional advantage of the U-shaped ferrule is that it provides a relatively low-profile to facilitate the design of smaller implantable medical devices.

Figure 1:
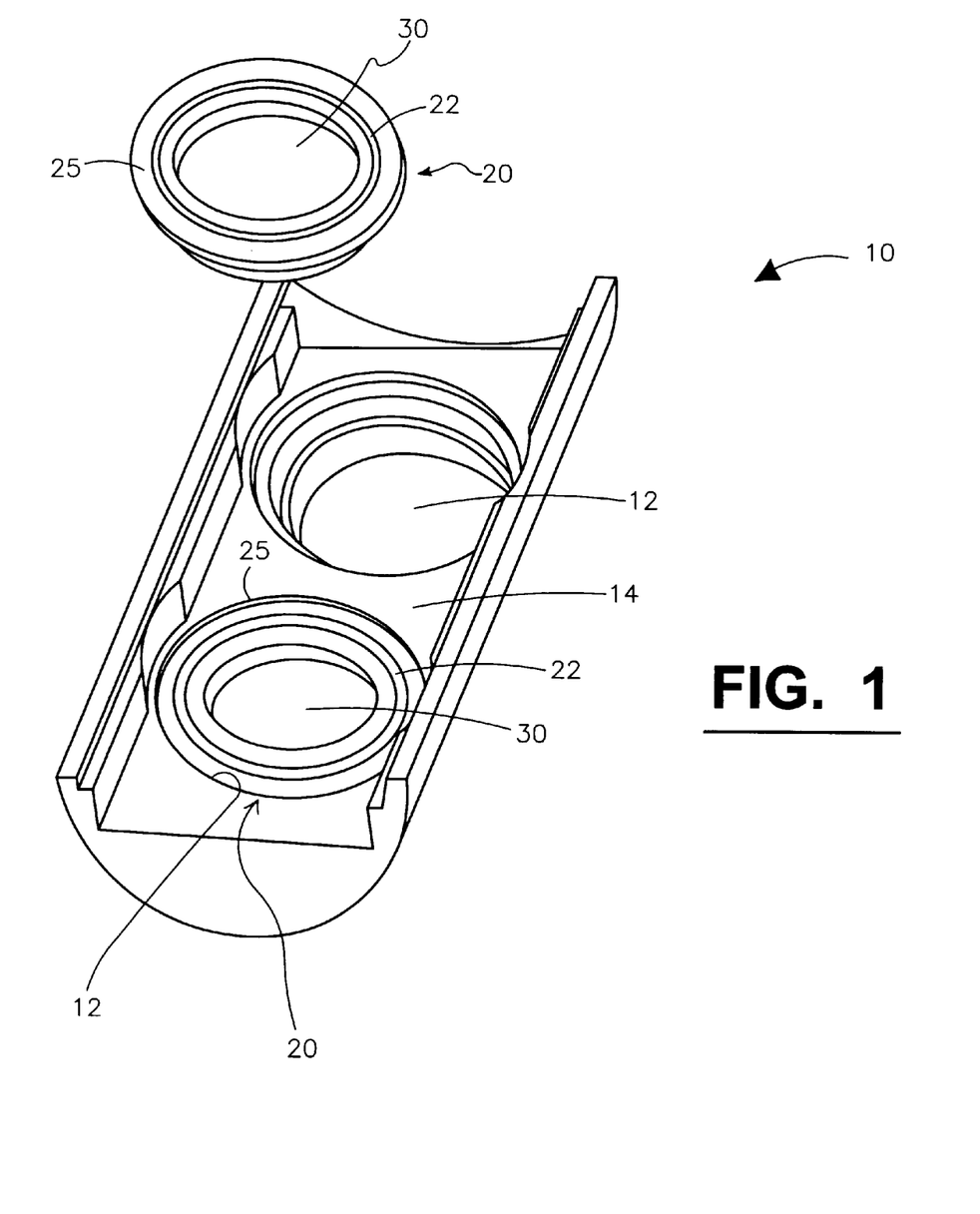
FIG. 1 is a perspective view of a portion of a device housing incorporating an optical window.

FIG. 1 is a perspective view of a portion of a housing incorporating two optical window assemblies according to the present invention. The depicted housing 10 includes two window openings 12 designed to accommodate an optical window assembly according to the present invention including a ferrule 20 and a lens 30 located within the ferrule 20. An optical window assembly is located in one of the window openings while another optical window assembly is depicted out of the other window opening 12.

It should be understood that optical window assemblies according to the present invention can be incorporated into a housing for use in any implantable medical device. As a result, they are preferably manufactured using biocompatible and biostable materials. Optical window assemblies according to the present invention may find particular use in connection with blood oxygen sensors implanted within a patient for long term monitoring of blood oxygen levels. As a result, the optical window assemblies of the present invention are preferably manufactured from biocompatible and biostable materials that are suited for long-term placement within the blood of a patient. Another application could include a feedthrough for electrical components in an implantable medical device.

One preferred material for the housing 10 and the ferrules 20 is titanium (Commercial grade 1 or 2), although other materials could be substituted for titanium. Examples of other suitable materials include, but are not limited to: stainless steel, platinum, niobium, etc.

Attachment of the ferrule 20 and lens 30 within the window openings 12 in the device housing 10 is typically accomplished by welding the ferrule 20 in place. The welding is typically performed using a laser directed at the surface 25 of the ferrules 20 and the adjoining surface 14 of the device housing 10 to form a hermetic seal between the ferrule 20 and the housing 10. Other welding processes, including but not limited to electron beam welding may also be used to weld the ferrule 20 in place.

Figure 2:
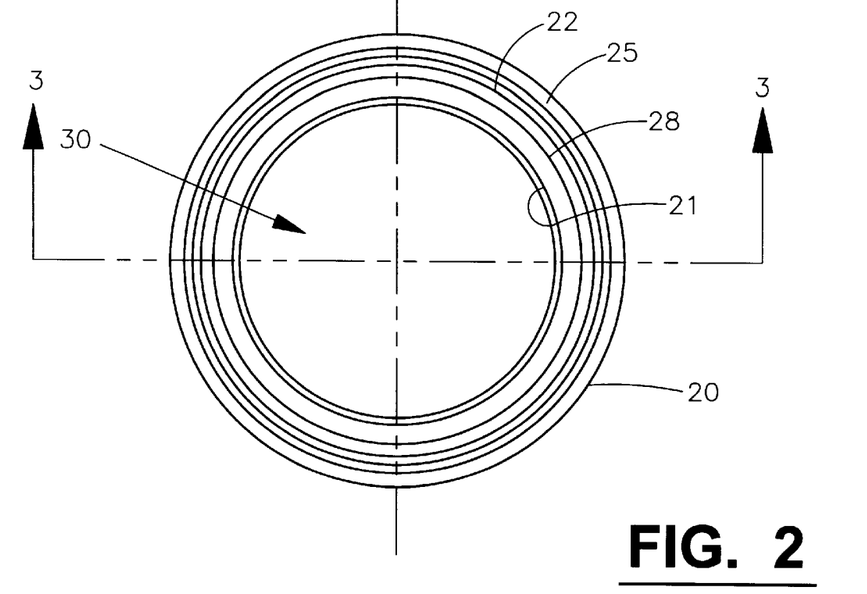
FIG. 2 is a plan view of one optical window assembly according to the preset invention.
Figure 3:
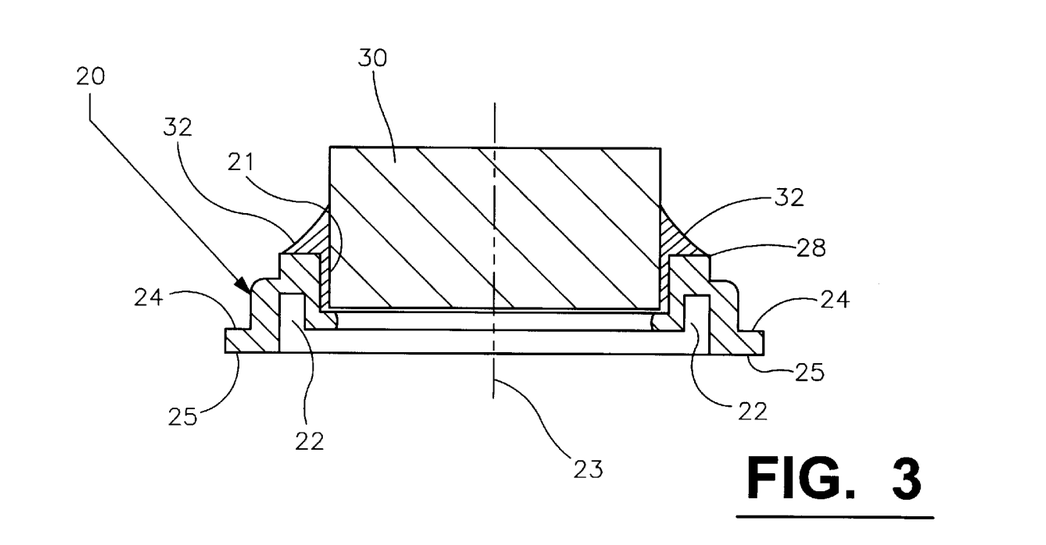
FIG. 3 is a cross-section of the optical window assembly of FIG. 2 taken along line 3—3 in FIG. 2.
Figure 4:
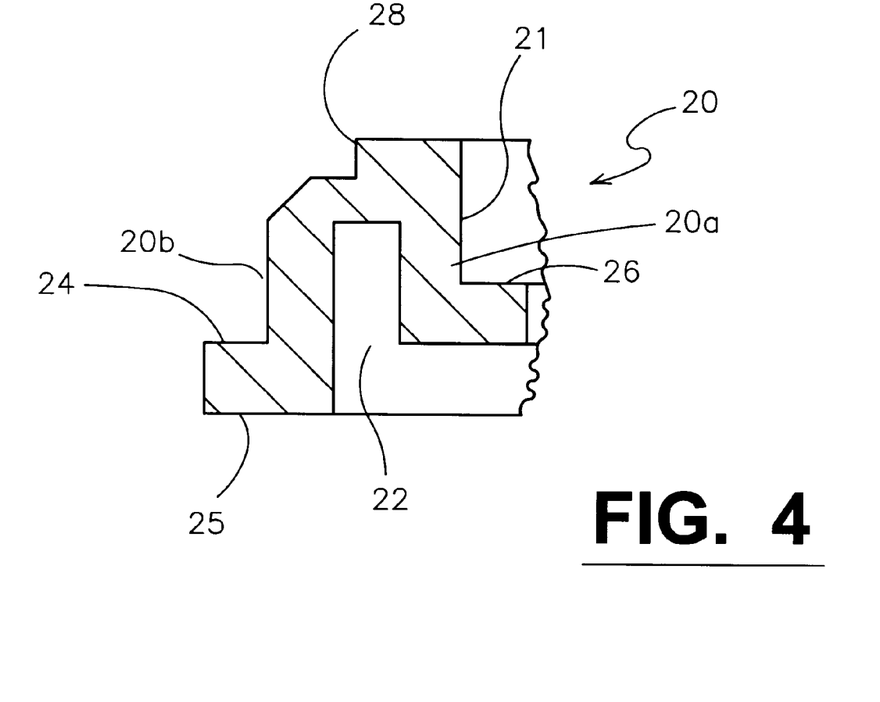
FIG. 4 is an enlarged cross-section of a ferrule used in an optical window assembly according to the present invention.

FIG. 2 is a plan view of one ferrule 20 and lens 30 for an optical window assembly according to the present invention. FIG. 3 is a cross-section of the ferrule 20 and lens 30 taken along line 3—3 in FIG. 2, and FIG. 4 is an enlarged partial cross-sectional view of the ferrule 20 alone. FIGS. 2–4 can be referred to during the following discussion of one preferred embodiment of an optical window assembly according to the present invention as described in more detail.

The depicted ferrule 20 preferably includes a body having a lens opening 21 in which lens 30 is located. The lens opening 21 is surrounded by a lens flange 26 which locates the lens 30 in its proper position with respect to the ferrule 20. After the lens 30 is in position within the ferrule 20, it is preferably maintained within the ferrule 20 by brazing. The brazing material 32 forms a fillet around the lens 30 as best seen in FIG. 3. The brazing material 32 also may wick between the lens 30 and ferrule 20 as also depicted in FIG. 3.

The brazing material preferably forms a hermetic seal between the lens 30 and the ferrule 20. As a result, the optical window assembly according to the present invention provides a hermetically sealed optical window for implantable medical devices by virtue of the hermetic seal between the housing 10 and ferrule 20 and the hermetic seal between the ferrule 20 and the lens 30.

The ferrule 20 also preferably includes a braze stop 28 adapted to prevent the brazing material 32 from flowing over the entire ferrule 20. Typically, the braze stop 28 will be a corner as shown or other sharp discontinuity in the surface of the ferrule 20 on which the brazing material 32 rests. That discontinuity 28 prevents the brazing material from flowing by virtue of the surface tension inherent in the flowable brazing material 32 during brazing.

The ferrule 20 also preferably includes a support flange 24 located around the outer perimeter of the ferrule 20. The support flange 24 is designed to rest against the window opening 12 in housing 10 to accurately locate surface 25 with respect to surface 14 for the welding process described above.

The ferrule 20 also includes a strain relief channel 22 located between the support flange 24 and lens opening 21 in the ferrule 20. The body of the ferrule 20 preferably has a generally U-shaped cross-section as depicted in FIG. 4 including an inner leg 20a and outer leg 20b with a strain relief channel 22 located between the legs. By providing a U-shaped profile through strain relief channel 22, the residual stresses (primarily in tension) that would be present in a solid ferrule (i.e., a ferrule without a strain relief channel) are reduced or eliminated by converting them into bending strain that is accommodated by the U-shaped ferrule body.

Figure 5:
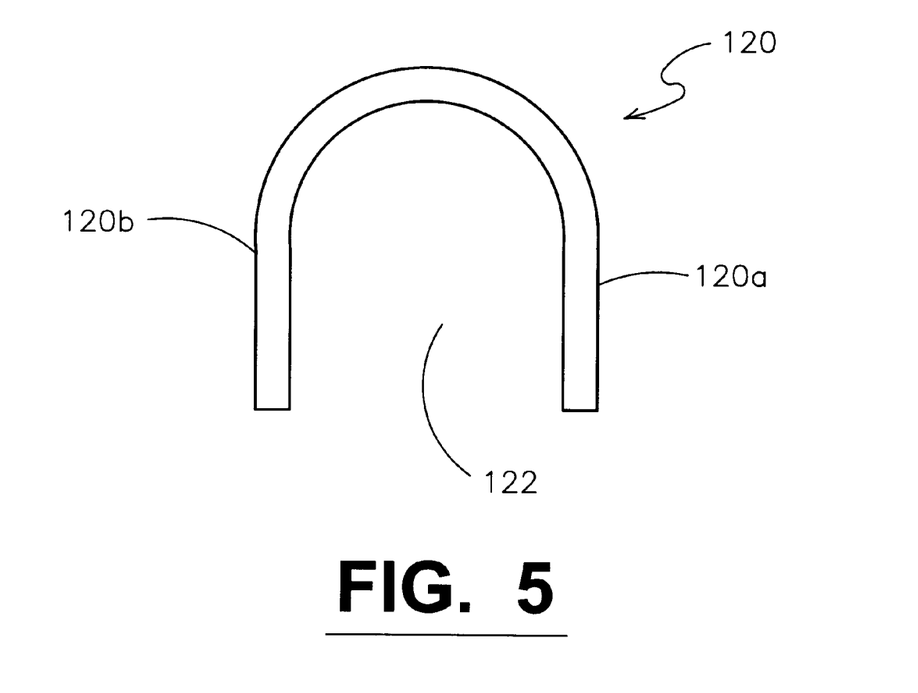
FIG. 5 is an enlarged cross-section of an alternative ferrule for an optical window assembly according to the present invention.

Although the ferrule 20 is shown as being formed with generally sharp corners, it should be understood that the ferrule 20 may also be formed with smoother, more rounded features. Typically, ferrules formed by stamping will have smoother contours than those formed by, e.g., machining. An example of such a ferrule 120 is depicted in an enlarged partial cross-sectional view in FIG. 5. The ferrule 120 includes an inner leg 120a and an outer leg 120b, as well as a strain relief channel 122 located between the legs 120a and 120b.

Those residual stresses in a solid ferrule, typically in tension, would normally be transmitted to the lens 30 and could cause the lens 30 to crack. A crack in the lens 30 can destroy hermeticity of the optical window assembly and may also affect the optical characteristics of the lens 30. By providing a ferrule 20 including a strain relief channel 22, however, the residual stresses from welding are converted into bending stresses that are at least partially, and preferably largely, compensated for in bending of the ferrule leg 20a relative to leg 20b. As a result, the stresses placed on the lens 30 after welding the ferrule 20 to the housing 10 are lowered to reduce or eliminate residual welding stresses as one cause of lens 30 cracking.

The lens 30 is preferably formed from sapphire, aluminum oxide grown with a single crystal lattice structure. Sapphire can be easily cut and polished to optical clarity without creating defects or cracks. If cracks or defects are present, they can be easily seen at low magnification. Sapphire is also biocompatible and biostable, including during long-term exposure in a blood environment. Although sapphire is the preferred material for the lens 30, it will be understood that the lens 30 could be provided of any appropriate material that provides the required biocompatible and biostable properties for long-term implantation. If the optical window assembly is to be used for transmitting optical energy, the material should transmit optical energy of the desired wavelengths (visible or invisible to the human eye). Where the optical window assembly is to be used to insulate a feedthrough pin, the lens material should be substantially electrically non-conductive.

The brazing material 32 used to maintain lens 30 within ferrule 20 can be composed of any suitable material or materials. Examples of suitable braze materials include, but are not limited to, gold, gold alloys, etc. One exemplary brazing material 32 is commercially pure gold (99.9% pure).

Typically, when the pure gold brazing material is used, the sapphire lens 30 must first be provided with a coating of niobium, titanium, or niobium/titanium alloy and a coating of a gold over the niobium or titanium in the areas where the brazed joint is to be formed. Various proportions of niobium and titanium may be co-sputtered to form the desired layer of a niobium/titanium alloy. These and other considerations regarding the brazing of sapphire lens 30 are discussed in International Publication No. WO 80/01620.

The methods of manufacturing an optical window assembly for an implantable medical device will now be described with reference to FIGS. 2–4. It is preferred that the first step involve formation of the ferrule 20. Where the ferrule 20 is constructed of titanium, one method of forming the ferrule 20 includes screw machining, although those skilled in the art will understand that many other techniques such as electron discharge machining (EDM), stamping, etc., may also be employed in the manufacture of the ferrules 20.

After formation of the ferrule 20, the lens 30 is preferably inserted into the lens opening 21 in the ferrule 20 as best seen in FIG. 3. After proper seating of the lens 30 within ferrule 20, brazing material 32 is applied between or at the junction between the ferrule 20 and lens 30. As is well known in the art of brazing, rings of the brazing material may be located about the joint to be brazed and the entire assembly, including the lens 30 and ferrule 20, and may be heated to the appropriate melting temperature of the braze material 32. It is, of course, preferable that any material for the brazing be chosen with a melting point substantially below that of either the ferrule 20 or lens 30 materials. Furthermore, care should be taken during brazing to avoid localized heating of the lens 30 that could result in cracking or other defects.

After the lens 30 is properly mounted in the lens opening 21 of the ferrule 20, the entire assembly of ferrule 20 and lens 30 can be inserted into a window opening 12 in a device housing 10 as seen in FIG. 1. Once properly located within the device housing 10, the ferrule 20 can be welded in place within the window opening 12 by use of a laser or any other appropriate welding technique as discussed above. It is preferred, but not essential, that the ferrule 20 be welded within device housing 10 because welding provides a joint having the desired hermeticity for the implantable medical device subject to long-term implantation in environments such as a blood environment.

The optical window assemblies according to the present invention can be used in a variety of implantable medical devices in which optical energy required to be transmitted into or out of a device housing located within a patient. The optical window assemblies may also find use in insulating feedthrough pins extending from the interior of an implantable medical device to its exterior or from the interior of a power source, e.g., an electrochemical cell, to the exterior of the power source.

Figure 6:
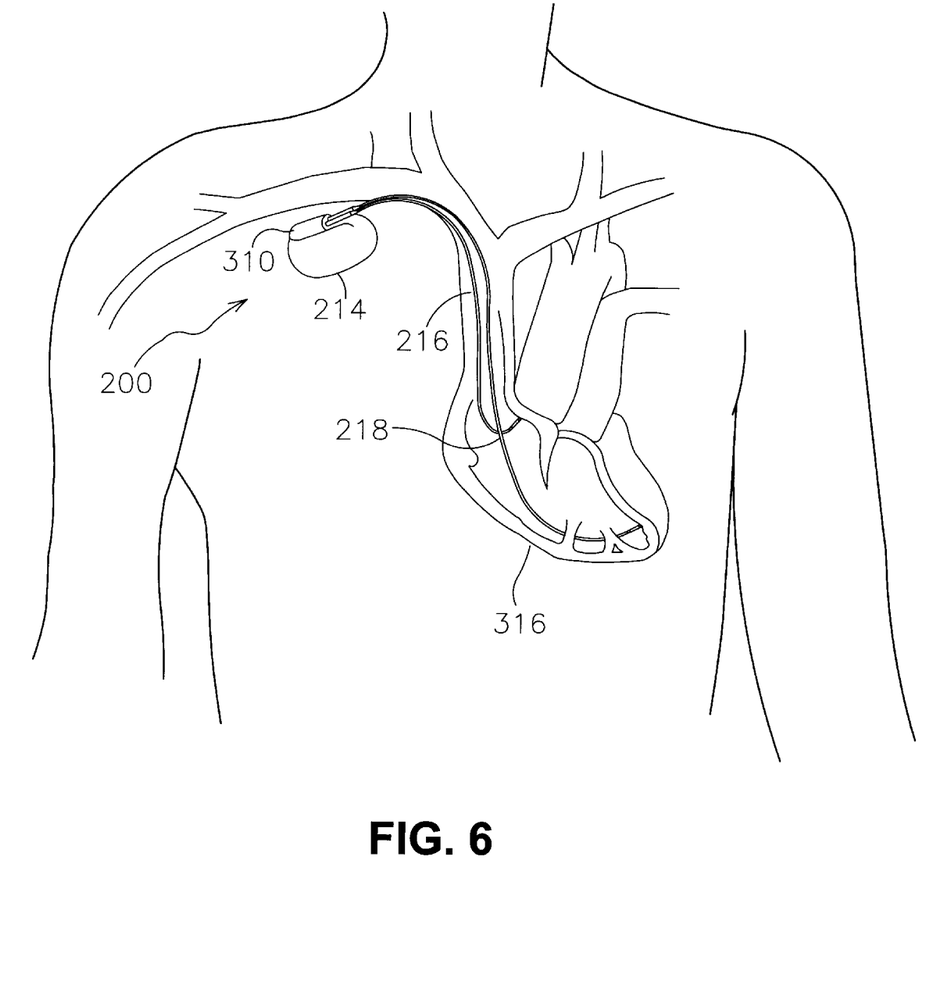
FIG. 6 is a simplified schematic view of an implantable medical device including an optical window assembly according to the present invention.

FIG. 6 is a simplified schematic view of an implantable medical device 200 embodying the present invention, where at least one improved pacing and sensing lead 216 or 218 is attached to an hermetically sealed enclosure 214 and implanted near human heart 316. In the case where implanted medical device 200 is a pacemaker it includes at least one or both of pacing and sensing leads 216 and 218. Pacing and sensing leads 216 and 218 sense electrical signals attendant to the depolarization and re-polarization of the heart 316, and provide pacing pulses for causing depolarization of cardiac tissue in the vicinity of the distal ends thereof. At least one of the leads 216 and 218 also preferably includes an oxygen sensor module along its length that includes one or more optical windows according to the present invention.

Implantable medical device 200 may be an implantable cardiac pacemaker such as those disclosed in U.S. Pat. No. 5,158,078 to Bennett et al, U.S. Pat. No. 5,312,453 to Shelton et al, or U.S. Pat. No. 5,144,949 to Olson, all hereby incorporated herein by reference in their respective entireties. Implantable medical device 200 may also be a PCD (Pacemaker-Cardioverter-Defibrillator) corresponding to any of the various commercially available implantable PCDs, with the substitution of pacing or sensing leads connector module 212 of the present invention for the connector block assembly otherwise present. The present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless or U.S. Pat. No. 4,821,723 to Baker et al., all hereby incorporated herein by reference in their respective entireties. Those devices may be employed directly in conjunction with the present invention, and most preferably are practiced such that the feedthroughs interconnecting the circuitry therein to their connector blocks is located to permit ready access between the feedthroughs and the electrical connectors disposed within the connector bores of connector or header module 212.

Alternatively, implantable medical device 200 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of implantable electrical device for use in conjunction with electrical leads, and is believed to be particularly advantageous in those contexts where multiple medical electrical leads are employed and desired.

In general, hermetically sealed enclosure 214 includes an electrochemical cell such as a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a micro-computer based system with AID conversion of sampled EGM amplitude values. The particular electronic features and operations of the implantable medical device are not believed to be of overriding significance in respect of practicing the present invention. One exemplary operating system is described in commonly assigned, co-pending U.S. patent application Ser. No. 08/678,219, filed Jul. 11, 1996, for "Minimally Invasive Implantable Device for Monitoring Physiologic Events," the disclosure of which is hereby incorporated by reference herein in its entirety.

It is to be understood that the present invention is not limited in scope to either single-sensor or dual-sensor pacemakers, and that other sensors besides blood oxygen, activity, and pressure sensors could be used in practicing the present invention. Nor is the present invention limited in scope to single-chamber pacemakers. The present invention may also be practiced in connection with multiple-chamber (e.g., dual-chamber) pacemakers.

Figure 7:
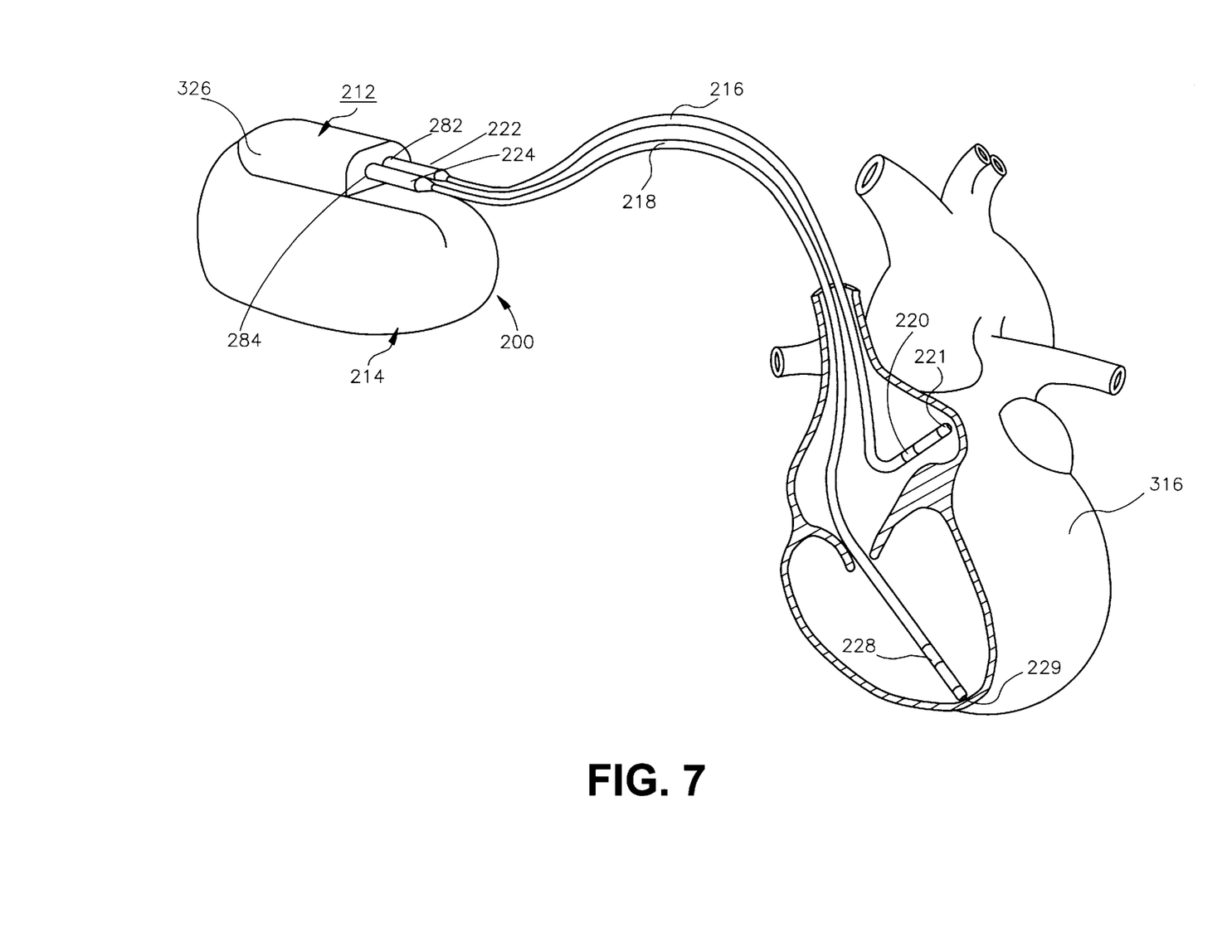
FIG. 7 is a schematic view of the device of FIG. 6 as it relates to a patient's heart.

FIG. 7 depicts connector module 212 and hermetically sealed enclosure 214 of implantable medical device or dual chamber pacemaker IPG 200 as they relate to patient's heart 316. Atrial and ventricular pacing leads 216 and 218 extend from connector header module 212 to the right atrium and ventricle, respectively. Atrial electrodes 220 and 221 disposed at the distal end of the atrial pacing lead 216 are located in the right atrium. Ventricular electrodes 228 and 229 at the distal end of ventricular pacing lead 218 are located in the right ventricle.

Figure 8:
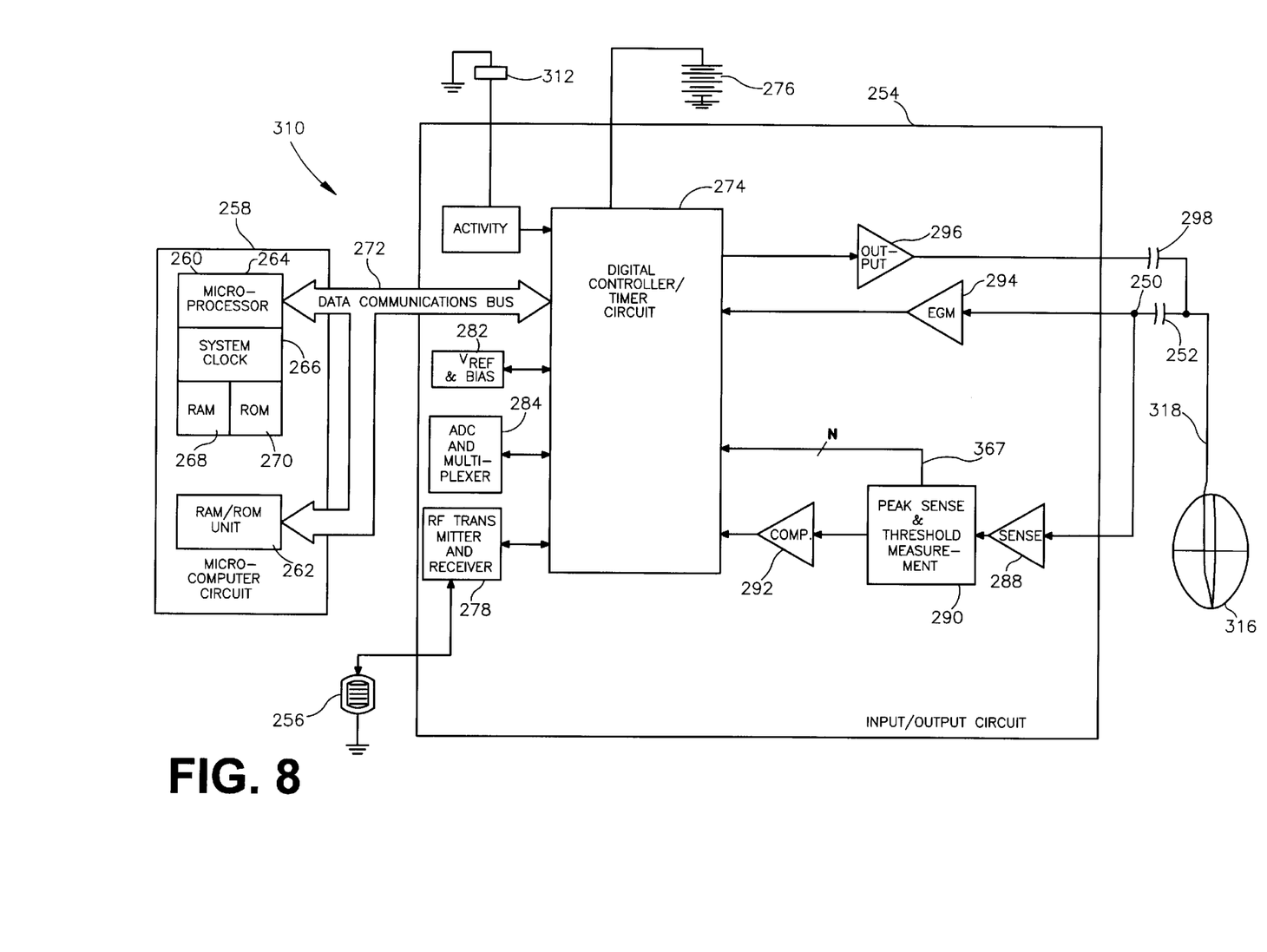
FIG. 8 is a block diagram illustrating some constituent components of a pacemaker in one embodiment of the present invention.

FIG. 8 shows a block diagram illustrating the constituent components of a pacemaker 310 in accordance with one embodiment of the present invention, where pacemaker 310 has a microprocessor-based architecture. The present invention may be utilized in conjunction with other implantable medical devices, however, such as cardioverters, defibrillators, cardiac assist systems, and the like, or in conjunction with other design architectures.

In the illustrative embodiment shown in FIG. 8, pacemaker 310 includes an activity sensor 312, which is preferably a piezoceramic accelerometer bonded to the hybrid circuit inside the pacemaker housing. Piezoceramic accelerometer sensor 312 provides a sensor output which varies as a function of a measured parameter that relates to the metabolic requirements of patient.

Pacemaker 310 of FIG. 8 is most preferably programmable by means of an external programming unit (not shown in the Figures). One such programmer suitable for the purposes of the present invention is the commercially available Medtronic Model 9790 programmer. The programmer is a microprocessor device which provides a series of encoded signals to pacemaker 310 by means of a programming head which transmits radio-frequency (RF) encoded signals to pacemaker 310 according to a telemetry system such as that described in U.S. Pat. No. 5,312,453 to Wyborny et al., the disclosure of which is hereby incorporated by reference herein in its entirety. It is to be understood, however, that the programming methodology disclosed in Wyborny et al. patent is identified herein for the illustrative purposes only, and that any programming methodology may be employed so long as the desired information is transmitted to and from the pacemaker. One of skill in the art may choose from any of a number of available programming techniques to accomplish this task.

Pacemaker 310 is schematically shown in FIG. 8 to be electrically coupled to a pacing lead 318 disposed in patient's heart 316. Lead 318 preferably includes an intracardiac electrode disposed at or near its distal end and positioned within the right ventricular (RV) or right atrial (RA) chamber of heart 316. Lead 318 may have unipolar or bipolar electrodes disposed thereon, as is well known in the art. Although an application of the present invention in the context of a single-chamber pacemaker is disclosed herein for illustrative purposes, it is to be understood that the present invention may equally well be applied in the context of a dual-chamber pacemakers or other implantable device.

Lead 318 is coupled to a node 250 in the circuitry of pacemaker 310 through input capacitor 252. In the presently disclosed embodiment, accelerometer 312 is attached to the hybrid circuit inside pacemaker 310, and is not shown explicitly in FIG. 8. The output from accelerometer 312 is coupled to input/output circuit 254. Input/output circuit 254 contains analog circuits for interfacing to heart 316, accelerometer 312, antenna 256, and circuits for the application of stimulating pulses to heart 316 to control its rate under control of software-implemented algorithms in microcomputer circuit 258.

Microcomputer circuit 258 preferably comprises on-board circuit 260 and off-board circuit 262. Circuit 258 may correspond to the microcomputer circuit disclosed in U.S. Pat. No. 5,312,453 to Shelton et al., the disclosure of which is hereby incorporated by reference herein in its entirety. On-board circuit 260 includes microprocessor 264, system clock circuit 266, and on-board RAM 268 and ROM 270. In the presently disclosed embodiment of the invention, off-board circuit 262 comprises a RAM/ROM unit. On-board circuit 260 and off-board circuit 262 are each coupled by a data communication bus 272 to a digital controller/timer circuit 274. Microcomputer circuit 258 may form a custom integrated circuit device augmented by standard RAM/ROM components.

The electrical components shown in FIG. 8 are powered by an appropriate implantable battery power source 276, in accordance with common practice in the art. For the sake of clarity, the coupling of battery power to the various components of pacemaker 310 is not shown in the Figures.

Antenna 256 is connected to input/output circuit 254 to permit uplink/downlink telemetry through RF transmitter and receiver unit 278. Unit 278 may correspond to the telemetry and program logic disclosed in U.S. Pat. No. 4,566,063 issued to Thompson et al., hereby incorporated by reference herein in its entirety, or to that disclosed in the above-referenced Wyborny et al. patent. The particular programming and telemetry scheme chosen is not believed to be critical for purposes of practicing the present invention so long as entry and storage of values of rate-response parameters are permitted.

$V_{REF}$ and Bias circuit 282 generates a stable voltage reference and bias currents for the analog circuits of input/output circuit 254. Analog-to-digital converter (ADC) and multiplexer unit 284 digitizes analog signals and voltages to provide "real-time" telemetry intracardiac signals and battery end-of-life (EOL) replacement function.

Operating commands for controlling the timing of pacemaker 310 are coupled by data bus 272 to digital controller/timer circuit 274, where digital timers and counters establish the overall escape interval of the pacemaker as well as various refractory, blanking and other timing windows for controlling the operation of the peripheral components disposed within input/output circuit 254.

Digital controller/timer circuit 274 is preferably coupled to sensing circuitry, including sense amplifier 288, peak sense and threshold measurement unit 290 and comparator/threshold detector 292. Circuit 274 is further preferably coupled to electrogram (EGM) amplifier 294 for receiving amplified and processed signals sensed by an electrode disposed on lead 318. Sense amplifier 288 amplifies sensed electrical cardiac signals and provides an amplified signal to peak sense and threshold measurement circuitry 290, which in turn provides an indication of peak sensed voltages and measured sense amplifier threshold voltages on multiple conductor signal path 367 to digital controller/timer circuit 274. An amplified sense amplifier signal is then provided to comparator/threshold detector 292. Sense amplifier 288 may correspond to that disclosed in U.S. Pat. No. 4,379,459 to Stein, which is hereby incorporated by reference herein in its entirety.

The electrogram signal provided by EGM amplifier 294 is employed when the implanted device is being interrogated by an external programmer (not shown) to transmit by uplink telemetric means a representation of an analog electrogram of the patient's electrical heart activity. See, for example, U.S. Pat. No. 4,556,063 to Thompson et al., hereby incorporated by reference herein in its entirety. Output pulse generator 296 provides pacing stimuli to patient's heart 316 through coupling capacitor 298 in response to a pacing trigger signal provided by digital controller/timer circuit 274 each time the escape interval times out, an externally transmitted pacing command is received, or in response to other stored commands as is well known in the pacing art. Output amplifier 296 may correspond generally to the output amplifier disclosed in U.S. Pat. No. 4,476,868 to Thompson, also incorporated by reference herein in its entirety.

While specific embodiments of input amplifier 288, output amplifier 296 and EGM amplifier 294 have been identified herein, this is done for the purposes of illustration only. The specific embodiments of such circuits are not critical to practicing the present invention so long as the circuits provide means for generating a stimulating pulse and are capable of providing digital controller/timer circuit 274 with signals indicative of natural or stimulated contractions of the heart.

An example of one implantable medical device 50 and associated lead 60 includes, but is not limited to a pacemaker and associated lead or leads. One potential location for the distal end of the lead 60 is in the heart of the patient, although other locations are also envisioned. The implantable medical device 50 could include oxygen sensing circuitry, as well as power sources and other components required for the device to perform its desired functions.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to implantable oxygen sensors, but could also be employed in any implantable medical device requiring an optical window for the transmission of optical energy therethrough or a feedthrough. The present invention further includes within its scope methods of making and using the optical windows described above.

What is claimed is:

1. An optical window assembly for a chronically implantable medical device comprising:
    a housing having a window opening therein;
    a ferrule mounted in the window opening, the ferrule comprising a ferrule body forming a lens opening, the ferrule body having a generally U-shaped cross-section with an inner leg, an outer leg, and a strain relief channel in the ferrule body between the inner leg and the outer leg, wherein outer leg of the ferrule body is proximate the window opening of the housing; and a lens mounted in the lens opening of the ferrule, wherein the lens is proximate the inner leg of the ferrule body.

2. An assembly according to claim 1, wherein the inner leg of the ferrule body further comprises a lens flange around at least a portion of the lens opening.

3. An assembly according to claim 1, wherein the outer leg of the ferrule body further comprises a support flange around at least a portion of the ferrule.

4. An assembly according to claim 3, wherein the support flange is connected to the window opening.

5. An assembly according to claim 1, wherein the lens is mounted in the lens opening with braze.

6. An assembly according to claim 5, wherein the ferrule body further comprises a braze stop to control flow of the braze.

7. An assembly according to claim 1, wherein the ferrule body comprises titanium.

8. An assembly according to claim 7, wherein the housing comprises titanium.

9. An assembly according to claim 8, wherein the housing comprises a blood oxygen sensor housing.

10. An assembly according to claim 1, wherein the window opening has a substantially circular shape.

11. An assembly according to claim 10, wherein the inner leg and outer leg of the ferrule body form concentric shapes located about the lens opening.

12. An assembly according to claim 11, wherein the strain relief channel has a shape which is concentric with the inner and outer legs of the ferrule body.

13. An assembly according to claim 1, wherein the lens comprises single crystal aluminum oxide.

14. A method of manufacturing an optical window for a chronically implantable medical device comprising:

providing a ferrule comprising a ferrule body forming a lens opening, the ferrule body having a generally U-shaped cross-section with an inner leg, an outer leg, and a strain relief channel in the ferrule body between the inner leg and the outer leg, wherein outer leg of the ferrule body is proximate the window opening of the housing;

mounting a lens in the lens opening of the ferrule, wherein the lens is proximate the inner leg of the ferrule body; and mounting the ferrule and lens in a window opening in a housing of the medical device, wherein the outer leg of the ferrule body is proximate the window opening in the housing.

15. A method according to claim 14, wherein the step of providing the inner leg of the ferrule body further comprises the step of providing a lens flange around at least a portion of the lens opening.

16. A method according to claim 14, wherein the step of providing the outer leg of the ferrule body further comprises the step of providing a support flange around at least a portion of the ferrule.

17. A method according to claim 14, wherein mounting the lens comprises brazing the lens in the lens opening.

18. A method according to claim 14, wherein mounting the ferrule comprises welding the outer leg of the ferrule body to the window opening.

19. A method according to claim 14, wherein the lens is mounted in the ferrule before the ferrule is mounted in the window opening.

20. A method according to claim 14, wherein the step of providing the housing further comprises the step of providing a blood oxygen sensor housing.

21. A method according to claim 14, wherein the step of providing the ferrule comprises screw machining the ferrule.

22. A method according to claim 14, wherein the step of providing the ferrule comprises stamping.

23. An implantable medical device including an optical window assembly comprising:

a housing having a window opening therein;

a ferrule mounted in the window opening, the ferrule comprising a ferrule body forming a lens opening, the ferrule body having a generally U-shaped cross-section with an inner leg, an outer leg, and a strain relief channel in the ferrule body between the inner leg and the outer leg, wherein outer leg of the ferrule body is proximate the window opening of the housing; and a lens mounted in the lens opening of the ferrule, wherein the lens is proximate the inner leg of the ferrule body.

24. An implantable medical device according to claim 23, wherein the inner leg of the ferrule body further comprises a lens flange around at least a portion of the lens opening.

25. An implantable medical device according to claim 23, wherein the outer leg of the ferrule body further comprises a support flange around at least a portion of the ferrule.

26. An implantable medical device according to claim 25, wherein the support flange is connected to the window opening.

27. An implantable medical device according to claim 23, wherein the lens is mounted in the lens opening with braze.

28. An implantable medical device according to claim 23, wherein the ferrule body further comprises a braze stop to control flow of the braze.

29. An implantable medical device according to claim 23, wherein the ferrule body comprises titanium.

30. An implantable medical device according to claim 23, wherein the housing comprises titanium.

31. An implantable medical device according to claim 23, wherein the housing comprises a blood oxygen sensor housing.

32. An implantable medical device according to claim 23, wherein the window opening has a substantially circular shape.

33. An implantable medical device according to claim 32, wherein the inner and outer legs of the ferrule body form concentric shapes located about the lens opening.

34. An implantable medical device according to claim 33, wherein the strain relief channel has a shape which is concentric with the inner and outer legs of the ferrule body.

35. An implantable medical device according to claim 23, wherein the lens comprises single crystal aluminum oxide.

* * * * *